United States Patent [19]

Kobayashi et al.

[11] Patent Number: 5,211,950
[45] Date of Patent: May 18, 1993

[54] STABILIZED CALCITONIN PHARMACEUTICAL COMPOSITION

[75] Inventors: Hideki Kobayashi; Seiji Mochizuki; Yuji Makino; Yoshiki Suzuki, all of Hino, Japan

[73] Assignee: Teijin Limited, Osaka, Japan

[21] Appl. No.: 527,461

[22] Filed: May 23, 1990

[30] Foreign Application Priority Data

May 23, 1989 [JP] Japan .................................. 1-127743

[51] Int. Cl.$^5$ .......................... A61K 9/14; A61K 9/48; A61K 9/52
[52] U.S. Cl. .................................... 424/422; 424/456; 424/489
[58] Field of Search ................ 514/926, 808; 424/456, 424/422, 489

[56] References Cited

U.S. PATENT DOCUMENTS

| | | | |
|---|---|---|---|
| 4,164,571 | 8/1979 | Bonfils | 514/926 |
| 4,241,051 | 12/1980 | Christie | 514/808 |
| 4,663,309 | 5/1987 | Kaiser | 514/808 |
| 4,690,952 | 9/1987 | Kagatani | 514/808 |
| 4,954,342 | 9/1990 | Lattanzi | 424/456 |

*Primary Examiner*—Thurman K. Page
*Assistant Examiner*—W. Bentson
*Attorney, Agent, or Firm*—Sughrue, Mion, Zinn, Macpeak & Seas

[57] ABSTRACT

A solid calcitonin pharmaceutical composition comprised of a therapeutically effective amount of calcitonins and ethylene diamine tetraacetates.

5 Claims, No Drawings

5,211,950

STABILIZED CALCITONIN PHARMACEUTICAL COMPOSITION

BACKGROUND OF THE INVENTION

1. Field of the Invention

The present invention relates to a calcitonin pharmaceutical composition having improved stability. More specifically, it relates to a solid calcitonin pharmaceutical composition having improved stability which includes calcitonins and ethylene diamine tetraacetates.

2. Description of the Related Art

Calcitonins are calcium regulating hormones secreted from the thyroid glands of mammals or the lateral thyroid glands of nonmammals. In chemical structure they correspond to single polypeptides including 32 amino acid residues. However, the arrangements of the amino acids differ among types of animals. In particular, there is a clear difference between mammalian calcitonins (mainly human calcitonin and swine calcitonin) and nonmammalian calcitonins (mainly salmon calcitonin and eel calcitonin).

In addition to these natural types of calcitonins, as nonnatural types, large numbers of derivatives and analogs are synthesized by removing, replacing, reversing, or otherwise treating one or more of the amino acid groups or arrays of natural calcitonins or by adding an N terminal group or C terminal group. Further, calcitonin gene related peptides are hormones existing in the brain, heart, etc. of mammals and are comprised of 39 amino acids with the 2nd position and seventh position cysteines bonded by S—S bonds.

These natural calcitonins and nonnatural calcitonins are referred to all together as calcitonins.

The action of these calcitonins is to reverse the effects of parathyroid hormones on the bones and kidneys. They have the action of inhibiting bone resorption and reducing blood calcium and the action of reducing blood serum phosphates. Therefore, animal calcitonin has been administered for the treatment of tumors, hyperparathyroidism, and grave hypercalcemia accompanying vitamin D poisoning. Further, they are suitable for treatment of infant cataplectic hypercalcemia, osteoporosis, Sudeck's atrophy, and Paget's disease. Further, calcitonin gene related peptides block the outflow of calcium stored in the cells from the cells. On the other hand, they do not block the inflow of calcium existing in the fluid outside the cells into the cells. In the coronary arteries, this mechanism eases the constriction of the muscles in the veins and reduces blood pressure. As a result of this action, usefulness is expected for the treatment of ischemic diseases of the brain or heart and high blood pressure or for the treatment of central nervous system diseases due to action as a neurotransmitter.

These useful calcitonins are supplied to the medical field as various preparations, but calcitonins are chemically unstable in the same general way as peptides, so there has been a desire for stabilized preparations with guaranteed potency.

In the past, as methods for stabilization of calcitonins, there have been known the method of freeze drying calcitonins and human albumin (Japanese Unexamined Patent Publication (Kokai) No. 63-5028) and the method of dispersion of calcitonins in gelatin and/or hydroxypropylmethylcellulose (Japanese Unexamined Patent Publication (Kokai) No. 61-282320).

On the other hand, contamination by microorganisms has become a problem in aqueous preparations containing calcitonins. To prevent this, there is known the method of adding benzalkonium chloride as a preservative (Japanese Unexamined Patent Publication (Kokai) No. 59-89619).

Furthermore, Japanese Unexamined Patent Publication (Kokai) No. 59-130820 discloses a liquid composition comprising a surfactant and calcitonin. This reference further discloses the optional use of disodium ethylenediamine tetraacetate as a preservative. However, this reference does not teach the advantageous effects of ethylenediamine tetraacetates for stabilizing calcitonins in a solid composition. Especially, the advantage effects obtained by the use of the ethylenediamine tetraacetates among the other preservatives are not taught in this reference.

While the stability of preparations of calcitonins stabilized by the above-mentioned methods is improved compared with the stability prior to the stabilization, it is still insufficient and the preparations must be refrigerated for storage. Therefore, there has been a desire for preparations of calcitonins having more improved stability.

Further, even among calcitonins, there are some non-natural types of calcitonins (for example, elcatonin) preparations made by chemically modifying parts of natural types of calcitonins to improve their stability which are improved in stability over preparations of natural types of calcitonin and can be stored at room temperature, but the stability cannot be said to be sufficient and there is a danger of reduction in activity when exposed to stringent conditions in distribution. Therefore, there has been a demand for preparations made even more stable in all types of calcitonins, both natural and nonnatural.

SUMMARY OF THE INVENTION

Accordingly, the objects of the present invention are to eliminate the above-mentioned disadvantages of the prior art and to provide a novel solid calcitonin pharmaceutical composition having improved stability.

Other objects and advantages of the present invention will be apparent from the following description.

In accordance with the present invention, there is provided a solid calcitonin pharmaceutical composition comprising a therapeutically effective amount of at least one calcitonin and at least one ethylene diamine tetraacetate, which is obtained by freeze drying an aqueous solution containing the calcitonin and the ethylene diamine tetraacetate or by adding a poor solvent to an aqueous solution containing the calcitonin and the ethylenediamine tetraacetate.

DESCRIPTION OF THE PREFERRED EMBODIMENTS

The present inventors engaged in in-depth studies on preparations of calcitonins with improved stability and, as a result, discovered that a calcitonin pharmaceutical composition containing calcitonins and ethylene diamine tetraacetates was remarkably improved in the stability of the calcitonins and that the effect of addition of the ethylene diamine tetraacetates could be observed even when the calcitonin pharmaceutical composition was in a solid (e.g., powder) form.

The inventors discovered that by making the calcitonins and the ethylene diamine tetraacetates a solid composition, the stability of the calcitonins in the calcitonin pharmaceutical composition including this solid composition could be remarkably improved, that the effect did not appear with simple physical mixtures of calcitonins and ethylene diamine tetraacetates, and that the effect was unique to ethylene diamine tetraacetate.

That is, regarding the discovery that a stabilization effect appears only when the calcitonins and ethylene diamine tetraacetate are prepared, by freezedrying of, or by poor solvent addition to, an aqueous solution of the calcitonins and the ethylenediamine tetraacetates, into a solid composition, a comparison was made of the heat stability of a composition obtained by dissolving calcitonins and ethylene diamine tetraacetates in water and freeze drying the result and a physical mixture of calcitonins and ethylene diamine tetraacetates as a control (Example 1 and Comparative Example 2 mentioned later). As a result, it was confirmed that there was a stabilizing effect on calcitonins only in the solid composition obtained by freeze drying.

Next, a comparison was made of the stability of the solid composition of calcitonins and ethylene diamine tetraacetates made by the same method as above with the stability of solid compositions of calcitonins and other compounds, in particular compounds reported as being effective for stabilization of calcitonins in the past (see Example 1 and Comparative Examples 3 to 8 mentioned later). As a result, it became clear that ethylene diamine tetraacetates were significantly more effective than conventionally known compounds for stabilizing calcitonins.

The reason why a solid composition of calcitonins and ethylene diamine tetraacetates exhibits superior stability is not clear. However, it is guessed that it is not because metals having a detrimental effect on the stability of calcitonins are captured by the chelating effect of the ethylene diamine tetraacetates. This is extremely important in terms of the novelty of the present invention. That is, a study was made of the stability of calcitonins in aqueous solutions and as a result it became clear that metal ions did not necessarily have anything to do with the stability (see Reference Example 1). Therefore, when preparing a solid composition of calcitonins and ethylene diamine tetraacetates, even though the ethylene diamine tetraacetates may capture metal ions coexisting in small amounts in the aqueous solution in which the two are dissolved, it is clear that this does not have anything to do with the solid composition obtained after freeze drying. The method of stabilization by adding ethylene diamine tetraacetates so as to capture metal ions and prevent oxidation, etc. is common knowledge and nothing novel, but special note should be made here that the stabilizing effect of ethylene diamine tetraacetates as in the present invention has nothing at all to do with the capturing of metal ions. On the other hand, it is known that ethylene diamine tetraacetates have a bactericidal and bacterial suppressive action. Further, it may be fully anticipated that peptide hormones such as calcitonins are consumed by bacteria and other microorganisms. Therefore, it may be guessed that the ethylene diamine tetraacetates in the solid composition act as an aseptic (i.e., preservative) through their bacterial suppressive effect, whereby the decomposition and consumption of calcitonins by microorganisms are prevented and thus the calcitonins stabilized. However, this was not found to be true in the later explained experiment (see Reference Example 2).

That is, there was a significant difference in stability between a sample (A) obtained by freeze drying an aqueous solution of calcitonins as is without sterilization through filtration and hermetically storing the resultant powdery substance and a sample (B) obtained by sterilizing an aqueous solution of calcitonins by filtration, then freeze drying the same and hermetically storing the powdery substance obtained, with the latter (B) having a higher stability, but the solid composition of the present invention obtained by sterilizing by filtration an aqueous solution of calcitonins and ethylene diamine tetraacetates, then freeze drying the result was even more stable than (B). That is, it was learned that ethylene diamine tetraacetates have a greater stabilizing effect in the sterilized state. In this way, it may be understood that the effect of ethylene diamine tetraacetates is not due to the aseptic (i.e., preservative). These facts and the fact that, as stated in Reference Example 1, ethylene diamine tetraacetates do not display stabilization in a mere physical mixture causes one to imagine some mutual action between ethylene diamine tetraacetates and calcitonins in the solid state. At the present time, the inventors are engaged in research into the nature of the stabilizing mechanism, but it will be understood from the above explanation that the solid composition is a novel composition not known in the past and has an effect which is novel and not based on the effects of ethylene diamine tetraacetates known in the past, so is a novel, useful discovery not achievable easily by a person skilled in the art.

As mentioned above, according to the present invention, the desired solid pharmaceutical composition can also be obtained by adding a poor solvent to the aqueous solution. Examples of such poor solvents are ethyl alcohol, acetonitrile, propylene glycol and glycerin.

As explained above, the present inventors engaged in in-depth research to provide a calcitonin preparation improved in stability and as a result discovered that a calcitonin pharmaceutical composition containing calcitonins and ethylene diamine tetraacetates stabilized the calcitonins, thus completing the present invention.

Therefore, the present invention lies in a calcitonin pharmaceutical composition including a therapeutically effective amount of calcitonins and ethylene diamine tetraacetates.

As the calcitonins used in the present invention, mention may be made of natural types of calcitonins and nonnatural types of calcitonins. As examples of natural types of calcitonins, mention may be made of mammalian calcitonins such as human calcitonin and swine calcitonin and nonmammalian calcitonins such as chicken calcitonin, salmon calcitonin, and eel calcitonin. As examples of nonnatural calcitonins, mention may be made of elcatonin. Further, as calcitonin gene related peptides, mention may be made of human calcitonin gene related peptides and swine calcitonin gene related peptides.

As the ethylene diamine tetraacetates used in the present invention, mention may be made of disodium ethylene diamine tetraacetate.

The amount of calcitonins in the calcitonin pharmaceutical composition of the present invention is difficult to generally stipulate by the form of the pharmaceutical composition and the volume of unit administration. More important is the amount of the ethylene diamine tetraacetates with respect to the calcitonins.

the amount of the ethylene diamine tetraacetates used in the present invention is 0.005 to 50 μg or so per 1 IU of the calcitonins, more preferably 0.02 to 0.5 μg per 1 IU of calcitonins.

The powdery calcitonin pharmaceutical composition including calcitonins and ethylene diamine tetraacetates in the present invention is prepared by making the calcitonins and ethylene diamine tetraacetates into a solid composition. The solid composition of the calcitonins and the ethylene diamine tetraacetates is obtained by dissolving the calcitonins and ethylene diamine tetraacetates in water, then freeze drying the aqueous solution or adding an organic solvent, causing precipitation and then drying. The calcitonins could conceivably change in nature due to organic solvents, so freeze drying is preferable. The solid compositions of calcitonins and ethylene diamine tetraacetates obtained in this way may be used as is as a powdery calcitonin pharmaceutical composition. Such a powderly calcitonin pharmaceutical composition may be used as a powder for injection or a powdery nasal administered preparation Further, it is possible to add other additives to make the powdery calcitonin pharmaceutical composition. In this case, the types and amounts of the additives would differ depending on the position of administration and the form of administration.

For example, in the case of a powder for injection of a type dissolved just before use, it is possible to add buffer agents, isotonics, analgesics, etc. to make the pharmaceutical composition. As a buffer agent, mention may be made of disodium hydrogen phosphate, sodium hydrogen phosphate, etc. As the isotonics, mention may be made of sodium chloride. As the analgesics, mention may be made of xylocaine. Further, in the case of a powdery nasal administered preparation, it is possible to add water-absorbing base, lubricants, etc., to make the pharmaceutical composition. As the water-absorbing base, there are crystalline cellulose, dextrin, methyl cellulose, hydroxypropyl cellulose, carboxymethyl cellulose, lactose, cross-linked polyacrylates, etc. As the lubricants, mention may be made of magnesium stearate. Further, in the case of a powdery eye drop preparation of the type dissolved just before use, it is possible to add the above-mentioned buffer agent, isotonics, etc. to make the pharmaceutical composition.

By such a powdery calcitonin pharmaceutical composition including calcitonins and ethylene diamine tetraacetates, a nasal administered preparation or powder for injection with stabilized calcitonins may be manufactured and provided for clinical use. The significance of this is very great.

when the powdery calcitonin pharmaceutical composition of the present invention is made a nasal administered preparation such as a gelatin capsule, it lightens the burden on patients using the calcitonins over long periods and therefore is preferable. In particular, when the form of the nasal administered preparation is a disposable administrator, it is convenient to carry, so this too is preferable. As such a disposable administrator, mention may be made of the one, for example, disclosed in WO89/01348.

EXAMPLE

The invention will now be explained using examples and reference examples so as to clarify the superior effects of the present invention, but the present invention is not limited by these in any way.

Example 1 and Comparative Examples 1 to 10

Two mg of salmon calcitonin (5,000 IU/mg) and 5 mg of disodium ethylene diamine tetraacetate (Dojin Kagaku Kenkyusho) were taken and 1 ml of purified water added to dissolve the same homogeneously, then this was distributed in test tubes and freeze dried to obtain the powdery composition of the present invention (Example 1). The content of the salmon calcitonin in the powderly composition was about 28.6%. The content of the salmon calcitonin after storage of the powdery composition at 40° C. and 25% RH for two weeks was determined by HPLC.

At the same time, the following powdery salmon calcitonin containing substances were prepared as comparative examples. First, 2 mg of salmon calcitonin (5000 IU/mg) was taken and dissolved by the addition of 2 ml of purified water, then this was freeze dried to obtain a powdery substance (Comparative Example 1). Further, 2 mg of salmon calcitonin (5000 IU/mg) and 5 mg of disodium ethylene diamine tetraacetate were taken and mixed fully in a mortar to obtain a homogeneous physical mixture as a powdery substance (Comparative Example 2). Further, the same method as in Example 1 was used except that instead of the disodium ethylene diamine tetraacetate, use was made of benzalkonium chloride (made by Nakaraitesk Co. (phonetic)), benzethonium chloride (Nakaraitest Co. (phonetic)), human albumin (ICN Immuno Biologicals Co.), sodium ascorbate (Wako Junyaku Co.), gelatin (DIFCO Co.), hydroxypropylmethyl cellulose (Shinetsu Kagaku Co.), sodium salt of methyl p-hydroxybenzoate (prepared from methyl p-hydroxybenzoate (Wako Junyaku Co.)) and sodium salt of thimerosal (Wako Junyaku Co.) to obtain powdery substances (Comparative Examples 3 to 10). These comparative examples were stored under the same conditions as in Example 1 to measure the residual rate (%) of the salmon calcitonin from the start of storage (content after storage compared with content before start of storage). A comparison was made with Example 1. The results are shown in Table 1.

TABLE 1

| Sample | Residual rate (%) of salmon calcitonin from start |
| --- | --- |
| Example 1 | 95 |
| Comparative Example 1 | 74 |
| Comparative Example 2 | 75 |
| Comparative Example 3 (benzalkonium chloride) | 35 |
| Comparative Example 4 (benzethonium chloride) | 55 |
| Comparative Example 5 (human albumin) | 83 |
| Comparative Example 6 (sodium ascorbate) | 15 |
| Comparative Example 7 (gelatin) | 84 |
| Comparative Example 8 (hydroxypropylmethyl cellulose) | 77 |
| Comparative Example 9 (sodium salt of methyl p-hydroxybenzoate) | 81 |
| Comparative Example 10 (sodium salt of thimerosal) | 71 |

Example 2

Two mg of salmon calcitonin (5,000 IU/mg) and 5 mg of disodium ethylene diamine tetraacetate (Dojin Kagaku Kenkyusho) were taken and 1 ml of purified water was added to dissolve the same homogeneously. Then, 4 ml of absolute ethanol was added to the solution to form white precipitate. This was filtered and washed with 2 ml of cold ethanol, followed by drying to obtain the powdery composition of the present invention (Example 2). The content of the salmon calcitonin in the powdery composition was 28.5%. This composition was stored at 40° C. and 25% RH for two weeks and the content of the salmon calcitonin was determined by HPLC after the storage. The remaining percent of the salmon calcitonin was 95%, which showed the comparable stability to that of Example 1.

Example 3

Production of Powdery Nasal Administered Preparation Including Salmon Calcitonin-EDTA Freeze Dried Composition Two mg of salmon calcitonin (5000 IU/mg) and 5 mg of disodium ethylene diamine tetraacetate were taken in a glass container and 1 ml of purified water added to homogenize the same, then this was freeze dried to obtain a homogeneous composition. Next, to the freeze dried composition was added 3 g of microcrystalline cellulose with 90% by weight or more of the particles having a particle size of 46 to 146 microns. This was mixed to obtain a powdery salmon calcitonin pharmaceutical composition for nasal administration. The powdery composition thus obtained contained in each 1 mg, 1.667 μg of disodium ethylene diamine tetraacetate and 3.334 IU of salmon calcitonin. The powdery composition was packed in about 30 mg amounts in hard gelatin capsules to obtain a nasal administered preparation which is opened during use to administer the powdery composition into the nose by a flow of air.

Example 4

Production of Powder for Injection for Dissolution Immediately Before Use Including Salmon Calcitonin and EDTA Two mg of salmon calcitonin (5000 IU/mg) and 5 mg of disodium ethylene diamine tetraacetate were taken and dissolved in 100 ml of injection use distilled water. This solution was filtered through a millipore filter (0.22 μ) and the filtrate distributed in 1 ml amounts in injection use vials. Next, these were freeze dried and sealed by rubber stoppers after completion of the freeze drying. The above operations were all performed in a sterile room. Next, the sealed vials were taken out of the sterile room and capped with aluminum to produce the powdery injection agents. Separately manufactured solution ampules (ampules of injection use distilled water containing buffer agent and isotonic) were attached to the powdery injection agents to make powdery injection agents for dissolution immediately before use.

Reference Example 1

Experiment Relating to Effects of Metal Ions on Stability of Calcitonins in Aqueous Solution One mg of salmon calcitonin (5000 IU/mg) was taken and dissolved in 10 ml of purified water. The resultant solution was filtered by a millipore filter (0.22 μ) and filled and sealed in ampules aseptically (A). The content of the salmon calcitonin in the liquid composition was measured by HPLC and as a result found to be 0.1 mg/ml. This was stored at 40° C. for 2 weeks, then the content of the salmon calcitonin measured again by HPLC.

On the other hand, in the same way as with the above sample (A), 1 mg of salmon calcitonin together with zinc chloride or magnesium chloride were dissolved together, then filtered and filled in ampules to make samples (B) and (C). These were stored at 40° C. and the residual rates of salmon calcitonin were compared with the above-mentioned sample (A). (Nota that the ion concentration of $Zn^{2+}$ and $Mg^{2+}$ was $5 \times 10^{-4}$ mole/liter.) The results are shown in Table 3.

TABLE 3

| Sample | Residual rate (%) of salmon calcitonin from start |
|---|---|
| A | 37 |
| B | 36 |
| C | 33 |

Reference Example 2

Reference Experiment Relating to Mechanism of Stabilizing Effect of Powdery Composition of Calcitonins and (thylene Diamine Tetraacetates Two mg of salmon calcitonin (5000 IU/mg) was dissolved in 2 ml of purified water and the solution was freeze dried as is to obtain the powdery substance (A). A solution of salmon calcitonin in purified water made in the same way was filtered by a millipore filter (0.22 μ) and the filtrate was freeze dried to obtain the powdery substance (B). Further, in the same way as Example 1, 2 mg of salmon calcitonin (5000 IU/mg) and 5 mg of disodium ethylene diamine tetraacetate (Dojin Kagaku Kenkyusho) were taken and homogeneously dissolved in 2 ml of purified water added thereto, then this was filtered by a millipore filter (0.22 μ) and the filtrate was freeze dried to obtain a powdery salmon calcitonin composition (C).

These three types of powdery substances or compositions were stored shut away from the outside at 40° C. for two weeks, then the contents of salmon calcitonin in the samples were measured by HPLC. The results are shown in Table 4.

TABLE 4

| Sample | Residual rate (%) of salmon calcitonin from start |
|---|---|
| A | 75 |
| B | 83 |
| C | 94 |

We claim:

1. A solid calcitonin pharmaceutical composition comprising a therapeutically effective amount of at least one calcitonin and at least one ethylene diamine tetraacetate in an amount of 0.005 to 50 μg per 1 IU of calcitonin, said composition being obtained either by freeze drying an aqueous solution containing said calcitonin and said ethylene diamine tetraacetate or by adding a poor solvent selected from the group consisting of ethyl alcohol, acetonitrile, propylene glycol and glycerin to an aqueous solution containing said calcitonin and said ethylene diamine tetraacetate.

2. A solic calcitonin pharmaceutical composition as claimed in claim 1, wherein the ethylene diamine tetraacetate is disodium ethylene diamine tetraacetate.

3. A solid calcitonin pharmaceutical composition as claimed in claim 1, having a form of a nasal administered preparation.

4. A solid calcitonin pharmaceutical composition as claimed in claim 3, wherein the form of the nasal administered preparation is a hard gelatin capsule.

5. A solid calcitonin pharmaceutical composition as claimed in claim 1, having a form of an injection agent or an eye drop for administration.

* * * * *